(12) United States Patent
Tweden

(10) Patent No.: US 6,250,305 B1
(45) Date of Patent: Jun. 26, 2001

(54) METHOD FOR USING A FLEXIBLE TRANSMYOCARDIAL IMPLANT

(75) Inventor: Katherine S. Tweden, Mahtomedi, MN (US)

(73) Assignee: HeartStent Corporation, St. Paul, MN (US)

( * ) Notice: Subject to any disclaimer, the term of this patent is extended or adjusted under 35 U.S.C. 154(b) by 0 days.

(21) Appl. No.: 09/009,400

(22) Filed: Jan. 20, 1998

(51) Int. Cl.[7] .................................................. A61B 19/00
(52) U.S. Cl. ............................................................ 128/898
(58) Field of Search ............................... 604/7–9; 623/1, 623/2, 66; 606/151, 197; 128/898

(56) References Cited

U.S. PATENT DOCUMENTS

| | | |
|---|---|---|
| 4,366,819 | 1/1983 | Kaster . |
| 4,546,499 | 10/1985 | Possis et al. . |
| 4,562,597 | 1/1986 | Possis et al. . |
| 4,769,031 | 9/1988 | McGough et al. . |
| 4,995,857 | 2/1991 | Arnold . |
| 5,409,019 | 4/1995 | Wilk . |
| 5,429,144 | 7/1995 | Wilk . |
| 5,452,733 | 9/1995 | Sterman et al. . |
| 5,655,548 | 8/1997 | Nelson et al. . |
| 5,755,682 * | 5/1998 | Knudson et al. .................. 604/8 |
| 5,797,933 * | 8/1998 | Snow et al. ...................... 606/151 |
| 5,944,019 | 8/1999 | Knudson et al. . |

OTHER PUBLICATIONS

Tea E. Acuff et al., Minimally Invasive Coronary Artery Bypass Grafting, 61 Ann. Thorac. Surg. 135–37 (1996).
Enio Buffolo et al., Coronary Artery Bypass Grafting Without Cardiopulmonary Bypass, 61 Ann. Thorac. Surg. 63–66 (1996).
Mark W. Connolly & Robert A. Guyton, Cardiopulmonary Bypass Techniques in Hurst's the Heart 2443–2450 (Robert C. Schlant & R. Wayne Alexander, eds. 8th ed. 1994).
Stuart W. Jamieson, Aortocoronary Saphenous Vein Bypass Grafting, in Rob & Smith's Operative Surgery: Cardiac Surgery, 454–470 (Stuart W. Jamieson & Norman E. Shumway, eds., 4th ed. 1986).
Ludwig K. Von Segesser, Arterial Grafting for Myocardial Revascularization: Indications, Surgical Techniques and Results 48–80(1990).
U.S. application serial No. 08/882,397 filed, Jun. 25, 1997.
U.S. application serial No. 08/944,313, filed Oct. 6, 1997.
Goldman, A. et al., "Experimental Methods for Producing a Collateral Circulation to the Heart Directly From the Left Ventricle", *J. Thoracic Surg.*, 31(3):364–374 (Mar. 1956).
Massimo, C. et al., "Myocardial Revascularization by a New Method of Carrying Blood Directly From the Left Ventricular Cavity into the Coronary Circulation", *J. Thoracic Surg.*, 34(2):257–264 (Aug. 1957).
Munro, I. et al., "The possibility of myocardial revascularization by creation of a left ventriculocoronary artery fistula", *Thoracic and Cardiovascular Surgery*, 58(1):25–32 (Jul. 1969).

* cited by examiner

Primary Examiner—David J. Isabella
(74) Attorney, Agent, or Firm—Merchant & Gould P.C.

(57) ABSTRACT

A transmyocardial implant includes a hollow conduit adapted to be inserted into and retained within the heart wall of a heart chamber containing oxygenated blood. The conduit is in blood-flow communication with blood contained within the chamber. A natural blood vessel graft having a first end is secured to the conduit for blood flow from the chamber to flow into the graft. The graft has a second end secured to the coronary vessel with an opening of the second end in blood flow communication with a lumen of the coronary vessel. The conduit and graft defining a blood flow path between the openings of the first and second ends.

16 Claims, 1 Drawing Sheet

METHOD FOR USING A FLEXIBLE TRANSMYOCARDIAL IMPLANT

BACKGROUND OF THE INVENTION

1. Field of the Invention

This invention pertains to an implant for passing blood flow directly between a chamber of the heart and a coronary vessel. More particularly, this invention pertains to a flexible transmyocardial implant.

2. Description of the Prior Art

Commonly assigned and co-pending U.S. patent application Ser. No. 08/882,397 filed Jun. 25, 1997, entitled "Method and Apparatus for Performing Coronary Bypass Surgery", and filed in the name of inventors Mark B. Knudson and William L. Giese, now U.S. Pat. No. 5,944,019 teaches an implant for defining a blood flow conduit directly from a chamber of the heart to a lumen of a coronary vessel. An embodiment disclosed in the aforementioned application teaches an L-shaped implant in the form of a rigid conduit having one leg sized to be received within a lumen of a coronary artery and a second leg sized to pass through the myocardium and extend into the left ventricle of the heart. As disclosed in the above-referenced application, the conduit is rigid and remains open for blood flow to pass through the conduit during both systole and diastole. The conduit penetrates into the left ventricle in order to prevent tissue growth and occlusions over an opening of the conduit.

Commonly assigned and co-pending U.S. patent application Ser. No. 08/944,313 filed Oct. 6, 1997, entitled "Transmyocardial Implant", and filed in the name of inventors Katherine S. Tweden, Guy P. Vanney and Thomas L. Odland, now U.S. Pat. No. 5,984,950 teaches an implant such as that shown in the aforementioned '397 application with an enhanced fixation structure. The enhanced fixation structure includes a fabric surrounding at least a portion of the conduit to facilitate tissue growth on the exterior of the implant.

Implants such as those shown in the aforementioned applications include a portion to be placed within a coronary vessel and a portion to be placed within the myocardium. The implants disclosed in the above-mentioned applications are rigid structures. Being rigid, the implants are restricted in use. For example, an occluded site may not be positioned on the heart in close proximity to a heart chamber containing oxygenated blood. To access such a site with a rigid, titanium implant, a very long implant must be used. A long implant results in a long pathway in which blood will be in contact with the material of the implant. With non-biological materials, such as titanium, a long residence time of blood against such materials increases the probability of thrombus. The risk can be reduced with anti-thrombotic coatings. Moreover, a rigid implant can be difficult to place while achieving desired alignment of the implant with the vessel. A flexible implant will enhance placement of the implant. Unfortunately, flexible materials tend to be non-biostable and trombogenic and may collapse due to contraction of the heart during systole.

SUMMARY OF THE INVENTION

According to a preferred embodiment of the present invention, a transmyocardial implant is disclosed for establishing a blood flow path through a myocardium between a heart chamber and a lumen of a coronary vessel residing on an exterior of the heart. The implant includes a hollow conduit adapted to be inserted into and retained within the heart wall of a heart chamber containing oxygenated blood. The conduit is in blood-flow communication with blood contained within the chamber. A natural blood vessel graft is secured to the conduit for blood from the chamber to flow into the graft. The graft is secured to the coronary vessel in blood flow communication with a lumen of the coronary vessel. The conduit and graft define a blood flow path between the heart chamber and the vessel.

DESCRIPTION OF THE PREFERRED EMBODIMENT

Figure 1:
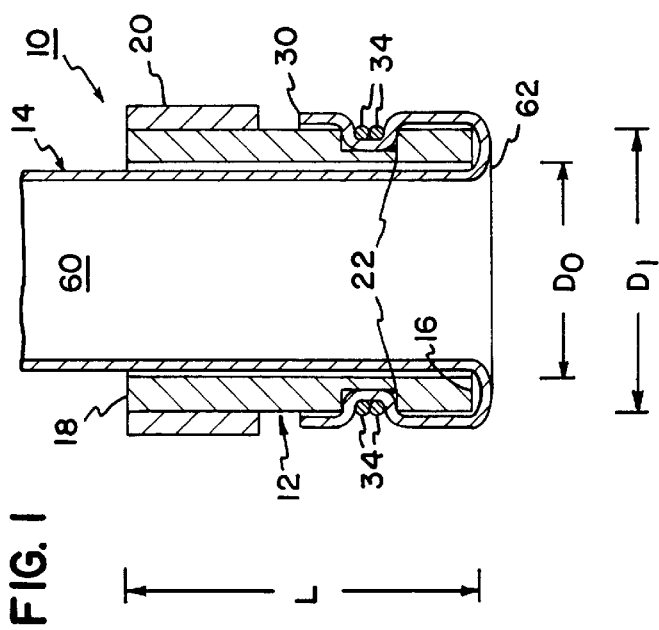
FIG. 1 is a side sectional view of an implant according to the present invention.

With initial reference to FIG. 1, an implant 10 is shown including a hollow, rigid cylindrical conduit 12 and a natural tubular graft vessel 14. The conduit 12 may be formed of titanium or other rigid biocompatible material such as pyrolytic carbon or may be titanium coated with pyrolytic carbon. The material of the conduit 12 is preferably a rigid material in order to withstand contraction forces of the myocardium. While the conduit 12 is described as a solid, rigid cylinder, the conduit 12 can be any structure (e.g., an expanded stent) suitable to hold open a path through the myocardium during both systole and diastole.

The conduit 12 is sized to extend through the myocardium 80 of the human heart to project into the interior of a heart chamber 82 (preferably, the left ventricle) by a distance of about 5 mm. By way of non-limiting example, the conduit 12 will have an axial length L of about 25–35 mm and an outside diameter $D_O$ of about 3 millimeters and an internal diameter $D_I$ of about 2 millimeters to provide a wall thickness of about 0.5 millimeters. The conduit 12 extends from a first end 16 to a second end 18. While not shown, the second end 18 of the conduit 12 may be provided with a flange to stop insertion of the conduit 12 into the myocardium 80. Such a flange will insure penetration of the second end 16 into the left ventricle 82 and will provide a convenient location for a surgeon to suture the conduit 12 to the myocardium. Adjacent to the lower end 16, the exterior wall of the conduit 12 is provided with a circumferential groove 22, the purpose of which will be described.

As discussed more fully in the afore-mentioned commonly assigned and co-pending U.S. patent application Ser. No. 08/944,313, the conduit 12 may be provided with tissue-growth inducing material 20 to further immobilize the conduit 12 within the myocardium 80. The material 20 is positioned adjacent upper end 18 and spaced from lower end 16 and groove 22. The material 20 surrounds the exterior of the conduit 12 and may be a polyester woven sleeve or sintered metal to define pores into which tissue growth from the myocardium 80 may occur.

The natural vessel 14 graft has first and second ends 30, 32. The first end 30 of the graft 14 is inserted through the interior of the conduit 12. The first end 30 is wrapped around the first end 16 of the conduit 12 such that the first end 30 of the graft 14 partially covers the exterior of the conduit 12 adjacent the first end 16 of the conduit 12 and covers the groove 22. The first end 30 of the graft 14 is secured to the conduit 12 by sutures 34 tightly placed around the exterior of the graft 14 overlying the groove 22.

The conduit 12 and attached graft 14 are placed in the myocardium 80 with the first end 16 protruding into the left ventricle 82. The implant 10 thus defines an open blood flow path 60 having a first end 62 in blood flow communication with the left ventricle 82. A second end 64 of the blood flow path 60 communicates directly with the lumen 84 of the coronary vessel 86 lying on an exterior of the heart wall 80. To bypass an obstruction in a coronary artery, the end 32 of the graft 14, is anastomosed to the artery 32 with sutures (not shown) as is done in conventional coronary artery bypass procedures. The end 32 is secured to the artery 86 distal to the obstruction.

Figure 2:
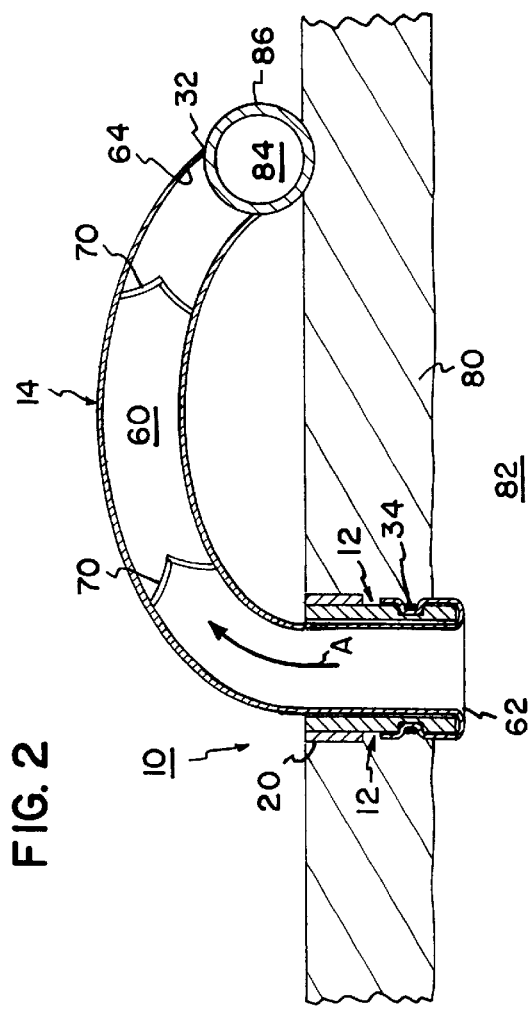
FIG. 2 is a side sectional view of an implant according to the present invention shown in place in a human heart wall with the implant establishing a direct blood flow path from a heart chamber to a coronary vessel.

With the above-described embodiment, the implant 10 permits revascularization from the left ventricle 82 to a coronary vessel such as a coronary artery (or a coronary vein in the event of a retrograde profusion procedure). The use of an elongated, flexible graft 14 permits revascularization where the vessel 86 is not necessarily in overlying relation to the chamber 82. For example, the implant 10 permits direct blood flow between the left ventricle 82 and a vessel 86 overlying the right ventricle (not shown). The use of a natural graft 14 results in blood flowing through path 60 being exposed only to natural biological material thereby reducing risk of thrombosis. As shown in FIG. 2, the graft 14 is wrapped around the conduit 12 so that no portion of the conduit 12 is in contact with blood within the left ventricle 82.

Any suitable graft may be used. For example, the graft 14 may be an artery or vein harvested from the patient. Such harvesting is common in traditional bypass surgeries. The present invention permits harvesting a much shorter length of vessel than would be otherwise required in conventional bypass surgeries. In addition to grafts harvested from the patient, other grafts could be used. These include cryopreserved grafts or bovine or umbilical vein glutaraldehyde treated vessels.

Certain veins, for example the saphenous vein, include natural valves 70. In the event such veins are selected as graft 14, the graft 14 is aligned so that the valves 70 are positioned to provide unobstructed flow from the left ventricle 82 to the vessel 86 as illustrated by arrow A in FIG. 2. The valves 70 act to obstruct reverse flow to the left ventricle.

Having disclosed the present invention in a preferred embodiment, it will be appreciated that modifications and equivalents may occur to one of ordinary skill in the art having the benefits of the teachings of the present invention. It is intended that such modifications shall be included within the scope of the claims which are appended hereto.

What is claimed is:

1. A method for performing a coronary bypass procedure at a coronary vessel lying at an exterior of a heart wall, the method comprising:

securing a first end of an elongated natural vessel graft to a rigid hollow conduit such that the graft and the conduit define a blood flow path, the conduit sufficiently rigid to maintain an open blood flow path through the conduit during systole;

inserting the hollow conduit through the heart wall such that the blood flow path is placed in fluid communication with a heart chamber; and securing a second end of the graft to the coronary vessel such that the graft extends at least partially on the exterior of the heart wall, the blood flow path defined by the conduit and the graft providing fluid communication between the heart chamber and the coronary vessel, wherein the blood flow path allows blood to flow from the heart chamber into the coronary vessel.

2. A method according to claim 1 wherein the coronary vessel is a coronary artery.

3. A method according to claim 1 wherein the first end of the graft is wrapped around an end of the conduit.

4. A method according to claim 1 wherein the graft has internal valves limiting flow to a direction from the first end to the second end.

5. A method according to claim 4 wherein the graft is a harvested saphenous vein.

6. A method according to claim 1 wherein a portion of the graft extends through the conduit.

7. A method according to claim 1 wherein the step of securing the second end of the graft to the coronary vessel comprises securing the second end of the graph to a side wall of the coronary vessel.

8. A method according to claim 3 wherein the first end of the graft folds over an end of the conduit.

9. A method according to claim 8 wherein the first end of the graft is held over the end of the conduit by a suture.

10. A method for performing a coronary bypass procedure at a coronary vessel lying at an exterior of a heart wall, the method comprising:

securing a first end of a natural vessel graft to a hollow conduit such that the graft and the conduit define a blood flow path;

inserting the hollow conduit through the heart wall such that the blood flow path is placed in fluid communication with a heart chamber;

folding a first end of the graft over an end of the conduit, the conduit having a groove, the first end of the graft being held over the end of the conduit by a suture positioned within the groove; and securing a second end of the graft to the coronary vessel such that the blood flow path defined by the conduit and the graft provides fluid communication between the heart chamber and the coronary vessel, wherein the blood flow path allows blood to flow from the heart chamber into the coronary vessel.

11. A method according to claim 1 wherein the conduit projects into an interior of the heart chamber.

12. A method for performing a coronary bypass procedure at a coronary vessel lying at an exterior of a heart wall, the method comprising:

securing a first end of a natural vessel graft to a hollow conduit such that the graft and the conduit define a blood flow path;

inserting the hollow conduit through the heart wall such that the conduit projects at least 5 mm into an interior of a heart chamber and the blood flow path is placed in fluid communication with the heart chamber;

securing a second end of the graft to the coronary vessel such that the blood flow path defined by the conduit and the graft provides fluid communication between the heart chamber and the coronary vessel, wherein the blood flow path allows blood to flow from the heart chamber into the coronary vessel.

13. A method for performing a coronary bypass procedure at a coronary vessel lying at an exterior of a heart wall, the method comprising:

providing a hollow conduit defining a blood flow path, the conduit including a rigid portion and a flexible portion, the rigid portion being sized to extend through the heart wall and being sufficient rigid to keep the blood flow path of the conduit open during systole;

inserting the rigid portion of the conduit through the heart wall into a heart chamber; and securing a free end of the flexible portion to the coronary vessel in an end to side anastomosis to direct blood flow from the heart chamber into the coronary vessel.

14. A method according to claim 13 wherein the flexible portion of the conduit extends through the rigid portion and folds over an end of the rigid portion.

15. A method according to claim 13 wherein the conduit projects into an interior of the heart chamber.

16. A method for performing a coronary bypass procedure at a coronary vessel lying at an exterior of a heart wall, the method comprising:

providing a hollow conduit defining a blood flow path, the conduit including a rigid portion and a flexible portion, the rigid portion being sized to extend through the heart wall and being sufficient rigid to keep the blood flow path of the conduit open during systole;

inserting the rigid portion of the conduit through the heart wall into a heart chamber such that the conduit projects at least 5 mm into the interior of the heart chamber; and securing a free end of the flexible portion to the coronary vessel in an end to side anastomosis to direct blood flow from the heart chamber into the coronary vessel.

* * * * *